United States Patent [19]

Cummings

[11] Patent Number: 4,659,787
[45] Date of Patent: Apr. 21, 1987

[54] METHOD FOR MAKING EPOXY CURING AGENTS

[75] Inventor: Lowell O. Cummings, San Anselmo, Calif.

[73] Assignee: Chemcrete International Partnership, Belmont, Calif.

[21] Appl. No.: 798,006

[22] Filed: Nov. 14, 1985

Related U.S. Application Data

[60] Division of Ser. No. 656,140, Sep. 28, 1984, Pat. No. 4,574,145, which is a continuation-in-part of Ser. No. 396,319, Jul. 8, 1982, Pat. No. 4,490,510.

[51] Int. Cl.[4] .................. C08G 8/28; C08L 61/24; C08L 61/34
[52] U.S. Cl. .................... 525/504; 525/509; 528/164; 528/262; 528/263
[58] Field of Search ............... 525/504, 509; 528/164, 528/262, 263

[56] References Cited

U.S. PATENT DOCUMENTS 3,931,110  1/1976  Freeman et al. ............... 525/504

*Primary Examiner*—John C. Bleutge
*Assistant Examiner*—Robert E. L. Sellers, II
*Attorney, Agent, or Firm*—Owen, Wickersham & Erickson

[57] ABSTRACT

A new class of epoxy curing agents has been discovered that utilizes the monomer of (a) urea-formaldehyde, (b) phenol modified urea-formaldehyde, or (c) thiourea-formaldehyde as the center of a polyamine molecule. The ether monomers are reacted with conventional aliphatic, cycloaliphatic, and aromatic polyamines to split off alcohol and water-yielding urea-formaldehyde etc., polyamine epoxy curing agents.

24 Claims, No Drawings

METHOD FOR MAKING EPOXY CURING AGENTS

This application is a division of application Ser. No. 06/656,140, filed Sept. 28, 1984, now U.S. Pat. No. 4,574,145, which is a continuation-in-part of application Ser. No. 396,319, filed July 8, 1982; now U.S. Pat. No. 4,490,510.

This inventionn relates to novel compounds useful as epoxy curing agents, to a method for making these new compounds.

A new class of epoxy curing agents has been discovered that utilizes the structure of urea-formaldehyde and also the structure of phenol-modified urea-formaldehyde as the center of a polyamine molecule. The amine groups are arranged around the urea-formaldehyde center in a radial fashion.

This may be represented as:

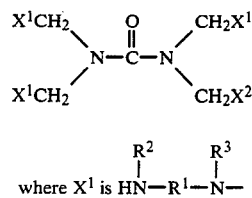

where $X^1$ is $HN-R^1-N-$ with $R^2$, $R^3$ and $X^2$ is either identical to $X^1$ or is

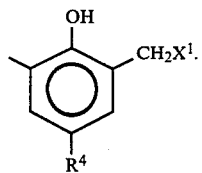

$R^1$, $R^2$, $R^3$, and $R^4$ are defined below.

This structure has a low amount of steric hindrance; that is, the structure of the molecule allows the most space between its components. This provides easy access for an epoxy molecule to react with these widely spaced amine groups.

The structures of these new compounds give a high degree of cross linking when reacted with epoxy resins and, therefore, contribute to the toughness and strength of the cured amine-epoxy resin.

Another advantage of incorporation of the urea-formaldehyde structure in the polyamine curing agent is that the curing agent is water-white in color, and so the subsequently cured amine-epoxy resin can be water-white. Urea-formaldehyde resins themselves are intrinsically colorless and resist becoming yellowish, and this same resistance to yellowing can be incorporated in the urea-formaldehyde polyamine structure.

The phenol-modified urea-formaldehyde resin have some yellowness, but are quite light.

Both the urea-formaldehyde polyamines and phenol-modified urea-formaldehyde polyamines can be low in cost, because urea, formaldehyde, and phenol are low-cost raw materials, and so are many of the polyamines.

Success in manufacturing these urea-formaldehyde polyamine curing agents depends, in part, on employing a process of urea-formaldehyde synthesis that produces largely monomeric urea-formaldehyde ether molecules.

One successful method of making urea-formaldehyde ether monomers is to react urea and paraformaldehyde in a low-molecular-weight alcohol, such as methanol at a ratio of urea molecules to formaldehyde molecules of one to four. This results in the following general structure:

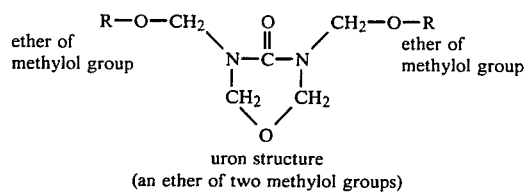

uron structure
(an ether of two methylol groups)

Here, R is a methyl, ethyl, propyl, or butyl radical. When R is a methyl radical the compound is N,N'-bis(-methoxymethyl)uron monomer; generalized the compound is N,N'-bis(alkoxy methyl)uron monomer (see U.S. Pat. No. 3,309,341).

Once this monomeric urea-formaldehyde ether molecule has been synthesized, it can be reacted directly with any of a number of polyamines including those that are presently utilized in the manufacture of amine curing agents. In this reaction about two to about four moles of the polyamine are reacted with each mole of the monomeric urea-formaldehyde ether molecule, taking care not to use two little amine such as would result in gelling.

A fundamental discovery of this invention is the discovery that polyamines or monoamines split the ether groups of the above urea-formaldehyde molecule. Then, one of the amine groups of the polyamine forms a carbon-nitrogen bond at the side of the ether splitting, giving off the reaction products of alcohol and water. For example:

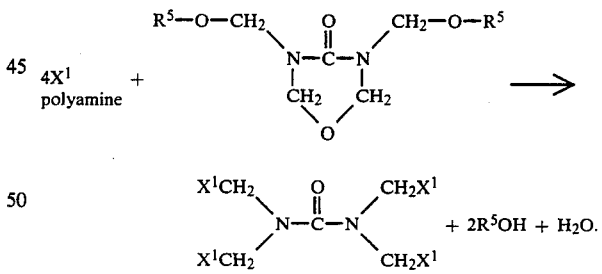

$R^5$ is a lower alkyl radical, having one to four carbon atoms.

This ease of splitting of these ether groups is somewhat surprising, because I had earlier found that the corresponding ether groups in a melamine formaldehyde resin are not split, under the same conditions.

As stated above, $X^1$ may be generalized as

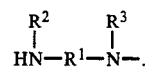

The following table shows the complete grouping of these radicals that can be $R^1$.

| | CHART FOR $R^1$ |
|---|---|
| Name of Polyamine Used to React with U-F Monomer, etc. | $R^1$ |
| (a) diethylene triamine | $-CH_2-CH_2-\underset{\underset{H}{\mid}}{N}-CH_2-CH_2-$ |
| (b) triethylene tetramine | $-CH_2-CH_2-\underset{\underset{H}{\mid}}{N}-CH_2-CH_2-\underset{\underset{H}{\mid}}{N}-CH_2-CH_2-$ |
| (c) hexamethylene diamine | $-CH_2-CH_2-CH_2-CH_2-CH_2-CH_2-$ |
| (d) polyoxypropylene diamines | $-CH(CH_3)-CH_2(-O-CH_2-CH(CH_3)-)_X$ |

X = 2.6 has M.W. (molecular weight) of 230 approx.
X = 5.6 has M.W. (molecular weight) of 400 approx.
Commercial Name:
Jeffamine D-230
Jeffamine D-400
Texaco Chemical Co.

| (e) polyoxypropylene triamine | $CH_3CH_2-\underset{\underset{CH_2(-O-CH_2CH(CH_3)-)_Z}{\mid}}{\overset{\overset{CH_2(-O-CH_2CH(CH_3)-)_X}{\mid}}{C}}-CH_2[O-CH_2CH(CH_3)]_Y-NH_2$ |
|---|---|

X + Y + Z = 5.3
M.W. of 400
Commercial Name:
Jeffamine T-403

| (f) poly(oxyethylene)diamine | $-\overset{\overset{CH_3}{\mid}}{C}HCH_2(-OCHCH_2-)_a(-OCH_2CH_2-)_b(-OCH_2CH-)_c\overset{\overset{}{}}{\underset{\underset{CH_3}{}}{}}$ with $CH_3$ groups |
|---|---| b = 13.5
a + c = 3.5
M.W. of 600
Commercial Name:
Jeffamine ED diamine

| (g) trimethyl hexamethylene diamine | $-CH_2-\underset{\underset{CH_3}{\mid}}{\overset{\overset{CH_3}{\mid}}{C}}-CH_2-\overset{\overset{CH_3}{\mid}}{C}H-CH_2-CH_2-$ |
|---|---|
| (h) N—aminoethyl piperazine | $-CH_2CH_2-N\underset{CH_2-CH_2}{\overset{CH_2-CH_2}{\diagup\diagdown}}N-$ (piperazine ring) |
| (i) 1,5 aminomethyl pentane diamine | $-CH_2CH_2CH_2CH_2\overset{\overset{}{}}{C}H-CH_3$ |
| (j) 2 methyl pentamethylene diamine | $-CH_2CH_2CH_2\overset{\overset{}{}}{C}H-CH_2-$ with $CH_3$ |
| (k) isophorone diamine | (cyclohexane ring with $CH_3$, $CH_3$, $H_2$, $H_2$, $CH_3$, $CH_2-$, and H substituents) |
| (l) 1,2-diamine cyclohexane | (cyclohexane ring with $H_2$, $H_2$, $H_2$, $H_2$, H, H substituents) |

-continued

CHART FOR R¹

| Name of Polyamine Used to React with U-F Monomer, etc. | R¹ |
|---|---|
| (m) xylene diamine | 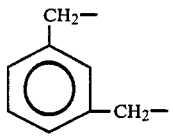 |
| (n) 2,4-bis(p-amino benzyl)aniline | 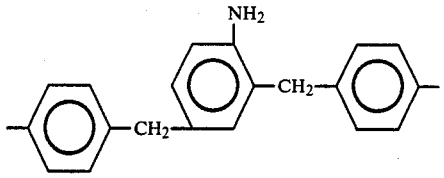 |
| an aromatic polyamine (o) BABA (du Pont), mixture principally of methylene dianiline | mixture of 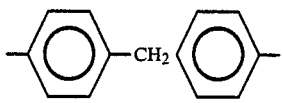 and |
| 2,4 bis(p-amino benzyl)aniline | 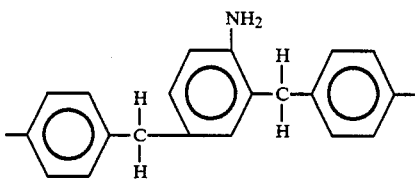 |
| (p) oleyl diamine |  |

For all of the amines (a) through (o) in the above table, $R^2$ and $R^3$ are both H. For the oleyl diamine, amine (p), either $R^2$ or $R^3$, but not both, is $C_{18}H_{35}$ and the other one is again H.

In the formula

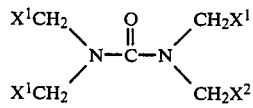

$X^1$ is as defined above, while
$X^2$ may either be identical to $X^1$ or may be

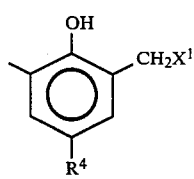

where $R^4$ is hydrogen or an alkyl radical with one to nine carbon atoms.

There are amine curing agents on the market that are made from phenol, formalin (a water solution of formaldehyde) and a polyamine. These have no relationship to the urea-formaldehyde polyamines of the present invention because they are made by a different chemical route, and have vastly different properties. The manufacture of these phenol-formaldehyde amines is illustrated by product Data Sheet 22-E-370-2-6 published by Veba-Chemie AG of Germany, which describes the reacting of phenol and 36% formalin using a basic catalyst. The polyamine is added to this water solution of the phenol-formaldehyde resin, and subsequently the water is driven off, resulting in a yellow viscous liquid.

As stated earlier, this resin is in no way related to the urea-formaldehyde polyamines of this invention, for no ether groups are formed in the water solution of phenol and formaldehyde under the above-stated basic conditions.

The urea-formaldehyde ether monomers may be made in an alcohol medium. The urea, paraformaldehyde (a solid form or polymer of formaldehyde having typically 91% formaldehyde content), and an alcohol, such as methanol, are first subjected to basic conditions under low heat such as 50° C. This belief alkaline reaction causes the paraformaldehyde to dissolve. Then the reaction is made strongly acidic, e.g., a pH of 2; at this time an exotherm takes place, as a result of the formation of ether groups, for ethers of urea-formaldehyde are only formed under acid conditions. The reaction is held at 70°–80° C. for a time in the order of one hour, to insure good ether formation. The monomer reaction is then finished by bringing the pH to 7.0. Another method of making these N,N'-bis(alkoxy methyl)urea monomers is detailed in U.S. Pat. No. 3,309,341.

There may be small amounts of methylol groups in these urea-formaldehyde ether monomers. These methylol groups react with the polyamine in the same manner as the ethers react.

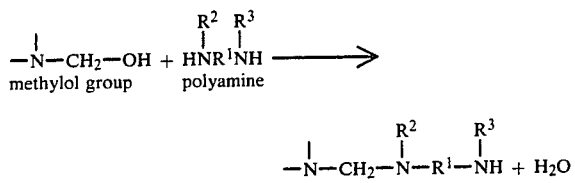

The formation of ether groups in the urea-formaldehyde resin can be followed by infrared spectrophotometry analysis. A sample of the reaction is scanned in an infrared spectroscopy instrument. The ether groups in urea-formaldehyde are shown by an infrared peak at 9.3 microns (1075 cm$^{-1}$). See the book *An Infrared Spectroscopy Atlas for the Coatings Industry*, 1980, Federation of Societies for Coating Technology, page 33.

This 9.3 micron peak develops soon after acidic conditions are made. The final urea-formaldehyde ether monomer has a very large 9.3 micron ether peak at the end of the reaction.

The progress of the reaction of the urea-formaldehyde ether monomer with the polyamine can be followed by noting that the ether peak is destroyed very soon after the urea-formaldehyde ether monomer is added to the polyamine. The finished reaction product has no trace of this 9.3 micron peak. The mixing of the urea-formaldehyde ether monomer into the polyamine is generally done at low temperature, such as 25° C. An exotherm takes place during the mixing which raises the temperature some 30° C. Then the alcohol and water of reaction are distilled off giving typically a water white, low viscosity, transparent liquid with remarkably good epoxy curing properties.

Some specific examples illustrate the formation of the urea-formaldehyde ether and related monomers and the reaction of the monomers with polyamines.

EXAMPLE 1

Urea-Formaldehyde Ether Monomer in Methanol

In a three liter glass flask fitted with a stainless steel paddle stirrer, thermometer, a pH electrode and a reflux condenser, is charged:

1200 g. methyl alcohol 99%
1200 g. 91% flake paraformaldehyde (corresponding to 1092 g. of 100% CH$_2$O=36.4 moles)
540 g. urea=9 moles.

This mix was stirred and heated to 40° C. The pH of this mix was 3.0. The pH was brought to 10.5 by the addition of a small amount of 40% sodium hydroxide. As the temperature rose to 55° C., the paraformaldehyde and the urea were dissolved, making a clear solution. At this point 50% H$_2$SO$_4$ was added to bring the pH to 2.5. This caused a mild exotherm, bringing the temperature to 78° C. The pH was maintained at 2.0–2.5, and the temperature was maintained at about 80° C. for about forty minutes. Then the pH was brought to 7.0 with NaOH. The cooled urea-formaldehyde solution had suspended Na$_2$SO$_4$ in it, which was filtered out leaving a water-white, transparent, low-viscosity liquid containing about 55% non-volatile urea-formaldehyde ether monomer. Infrared analysis showed a strong peak at 9.3 microns, indicating ethers of methylol groups.

EXAMPLE 2

Thiourea-Formaldehyde Ether Monomer in Methanol

It has been found that thiourea

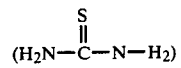

readily reacts in the same manner as urea in making the monomer.

In a 500 ml. flask fitted with a stainless steel paddle stirrer, thermometer, a pH electrode and reflux condenser, was charged:

One mole, 76 g. thiourea, crystals, 99%
Four moles, 132 g. 91% flake paraformaldehyde (corresponding to 120 g. of 100% CH$_2$O) 200 g. methyl alcohol 99%.

This mix was stirred and heated to about 40° C. The pH of this mix was 5.2. The pH was brought to 11.1 by the addition of a small amount of 40% sodium hydroxide. As the temperature rose to 60° C., the paraformaldehyde and thiourea dissolved making a clear solution. At this point 50% H$_2$SO$_4$ was added to bring the pH to 2.5. This caused a mild exotherm bringing the temperature to 70° C. This mix was stirred for one hour maintaining the temperature at 65° to 70° C.

During this time the pH spontaneously fell to 1.65. Then the pH was brought to 7.0 with NaOH. The cooled thiourea-formaldehyde solution had suspended Na$_2$SO$_4$ in it, which was filtered out leaving a water-white, transparent low-viscosity liquid containing about 48% non-volatile thiourea-formaldehyde ether monomer.

EXAMPLE 3

Composite Urea-Nonyl-Phenol Formaldehyde Ether Monomer

In a 500 ml. glass flask fitted with a stainless steel paddle stirrer, thermometer, pH electrode, and reflux condenser, the following ingredients were added:

0.5 mole, 110 g. nonyl phenol
0.5 mole, 30 g. urea
3.03 mole, (100 g. of 91% paraformaldehyde corresponding to 91 g. 100% CH$_2$O) 250 g. isopropyl alcohol, 99%.

This mix was heated and stirred while 40% NaOH was added to bring the pH from 2.5 to 11.0. At 85° C. the paraformaldehyde and urea were dissolved to make a clear solution. Then 50% H$_2$SO$_4$ was added to bring the pH to 1.2. A mild exotherm took place, causing some refluxing. The temperature was maintained at about 70° C. for an hour while the pH was held at or near 1.2. Then NaOH was used to bring the pH to 7.0. The filtered solution was a light yellow transparent solution containing about 47% urea-nonyl phenol formaldehyde ether monomer. A large infrared peak at 9.3 microns indicated ethers of methylol groups.

EXAMPLE 4

Composite Urea-Phenol Formaldehyde Ether Monomer

In a one liter glass flask fitted with a stainless steel paddle stirrer, therometer, pH electrode and reflux condenser, the following ingredients were added:

|   |         |                                          |
|---|---------|------------------------------------------|
|         | 300 g.  | methyl alcohol 99%                       |
| 2 moles,| 188 g.  | phenol, U.S.P.                           |
| 1 mole, | 60 g.   | urea                                     |
| 3 moles,| 99 g.   | 91% paraformaldehyde, (corresponding     |
|         | to 90 g.| 100% CH$_2$O).                           |

The mix was stirred and heated while 40% NaOH was added to bring the pH from 6.5 to 9.5. At 50° C. the paraformaldehyde dissolved, forming a transparent, slightly yellow liquid. Then 50% H$_2$SO$_4$ was added to bring the pH to 2.1. An exotherm took place, bringing the temperature from 52° to 68° C. The pH dropped to 1.0. The temperature was maintained at 64° C. for ten minutes and the pH was brought from 1.0 to 7.0 with NaOH.

The cooled solution had some white precipitate which was filtered off, leaving a water-white, transparent solution. Infrared analysis showed a strong urea carbonyl peak at 6.05 microns and a large ether peak at 9.3 microns. The solution had about 50% non-volatile urea-phenol formaldehyde ether monomer.

EXAMPLE 5

Urea-Formaldehyde Ether Monomer Reacted with an Aromatic Polyamine

The urea-formaldehyde ether monomer of Example 1, in an amount of 85 grams (47.5 grams of non-volatiles, i.e., 1 equivalents), is reacted with 1 mole (304 grams) of du Pont BABA, having a composition, weight percent:

| | |
|---|---|
| p,p-methylene dianiline | 3–10% |
| 2,4-bis(p-aminobenzyl) aniline (triamine) | 70–80% |
| tetramine | 10–80% |
| higher amines | 1. |

The aromatic polyamine was heated and stirred in a flask to 100° C. and the urea-formaldehyde ether monomer was added over 20 min. time and the temperature had climbed to 125° C.

Then 50 g. of benzyl alcohol was added to reduce the viscosity of this thick red brown liquid with a whitish crust on top. Methanol was distilled off during this time. Subsequently the whitish crust was dispersed in the red brown liquid and the crust dissolved into the main liquid giving a transparent viscous liquid at 150° C.

This liquid solidified as a dark red-brown brittle solid at about 90° C., considerably higher than the starting polymethylene dianiline. There was a urea carbonyl peak shown in infrared analysis of the final product at about 6.05 microns. This was not present in the starting polymethylene dianiline. The infrared peak at 6.05 microns indicated that a compound had been formed between the polymethylene dianiline and the urea-formaldehyde ether monomer.

Examples of the reaction of the urea-formaldehyde ether and related monomers with polyamines All reactions were done in a glass flask fitted with paddle stirrer, therometer, addition funnel and a distillation condenser. In all cases the polyamine was stirred in the flask at room temperature, while the urea-formaldehyde either or related monomer solution in alcohol was added to the polyamine. If the opposite addition was done,—i.e., adding the polyamine to the urea-formaldehyde ether solution—a gel would result in a short time. A substantial exotherm results from the addition of the monomer solution etc. to the polyamine during the ten to twenty minutes addition time. Slow addition is important, for too-rapid addition can result in some gel particles.

After the addition of the monomer was complete, alcohol and water were distilled off from the urea-formaldehyde polyamine or related polyamine. Some distillations were at atmospheric pressure where the residue temperature was 130° C. Other distillations were done under reduced pressure of about 25 inches of vacuum where the temperature was 75° C.

In the following table urea-formaldehyde ether is abbreviated to UF, urea-formaldehyde ether monomer to UFM, and urea-phenol-substituted-formaldehyde ether to UPFM.

Note that in Example 7, the mole ratio of polyamine to UFM is about 2.66. Mole ratios much lower than about four result in formulations like this or similar to it, sometimes in mixtures with the four-to-one structure shown above:

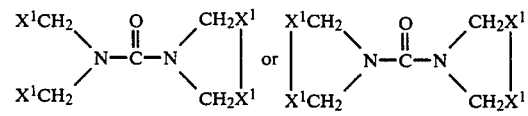

TABLE I

| Example No. | UFM OR UPFM | Polyamine | Properties of the UF Polyamine Color of Liquid | Viscosity at 25° C. in Poises |
|---|---|---|---|---|
| 6 | 130 g. UFM of Example 1<br>= 72 g. non-volatile<br>= 1.5 equivalents | 155 g. diethylene triamine<br>1.5 moles | water white transparent | 1.2 |
| 7 | 260 g. UFM of Example 1<br>= 143 g. non-volatile<br>= 3 equivalents | 206 g. diethylene triamine<br>2.0 moles | water white transparent | 2.15 |
| 8 | 85 g. UFM of Example 1<br>= 47.5 g. non-volatile<br>= 1 equivalent | 146 g. triethylene tetramine<br>1.0 mole | light yellow transparent | 2.4 |
| 9 | 167 g. UFM of Example 1<br>= 92 g. non-volatile<br>= 1.93 equivalents | 486 g. 70% solution of hexamethylene diamine in H$_2$O<br>= 340 g. non-volatile<br>= 2.93 moles (Here there is excess which does not react with the UFM.) | water white transparent; when cooled to 15° C., some white crystals formed but melted at 25° C. | about 1 |
| 10 | 260 g. UFM of Example 1 | 500 g. 70% solution of | water white transparent | 3.4 |

TABLE I-continued

| Example No. | UFM OR UPFM | Polyamine | Color of Liquid | Viscosity at 25° C. in Poises |
|---|---|---|---|---|
| | = 144 g. non-volatile<br>= 3.04 equivalents | hexamethylene diamine in H₂O<br>= 350 g. non-volatile<br>= 3.20 moles | | |
| 11 | 170 g. UFM of Example 1<br>= 95 g. non-volatile<br>= 2.0 equivalents | { 100 g. Jeffamine D-400<br>polyoxypropylene<br>diamine MW 400<br>= 0.25 mole<br>290 g. 70% solution of<br>hexamethylene diamine<br>in H₂O<br>= 203 g. non-volatile<br>= 1.75 moles } | water white transparent | 1.8 |
| 12 | 85 g. UFM of Example 1<br>= 47.5 g. non-volatile<br>= 1 equivalent | 230 g. Jeffamine D-230<br>polyoxypropylene diamine<br>M W 230 | very slightly yellow transparent | 3.3 |
| 13 | 170 g. UFM of Example 1<br>= 95 g. non-volatile<br>= 2 equivalents | 122 g. monoethanol amine<br>= 2 moles (Note this usable (monoamine.) | light yellow transparent | 11.2 |
| 14 | 200 g. UPFM of Example 3<br>urea-nonyl phenol<br>formaldehyde monomer<br>= 94 g. non-volatile<br>=1.2 equivalents | 164 g. 85% solution of<br>hexamethylene diamine in H₂O<br>= 140 g. non-volatile<br>= 1.2 moles | light yellow transparent | about 1.5 |
| 15 | 160 g. UPFM of Example 3<br>= 77 g. non-volatile<br>= 1.0 equivalent | 160 g. Adogen 572<br>(oleyl diamine)<br>= 1.0 equivalent | light tan-yellow translucent | 1.1 |
| 16 | 300 g. UPFM of Example 4<br>= 150 g. non-volatile | 300 g. 70% solution of<br>hexamethylene diamine in H₂O | light yellow transparent | about 1.5 |
| 17 | 65 g. UFM of Example 1 | 300 g. Jeffamine T403 | water-white sl. cloudy | 10.8 |
| | = 36 g. non-volatile<br>= 0.75 equivalent | [ polyoxypropylene<br>triamine MW 400 ]<br>0.75 mole | | |
| 18 | 43 g. UFM of Example 1<br>= 24 g. non-volatile<br>= 0.5 equivalent | 300 g. Jeffamine ED-600<br>[poly(oxyethylene) diamine]<br>mol. wt. 600 | water white transparent | 11 |
| 19 | 172 g. UFM of Example 1<br>= 95 g. non-volatile<br>= 2 equivalents | 340 g. isophorone diamine<br>= two moles<br>a product of Huels,<br>formerly Veba | water-white transparent | 33 |
| 20 | 172 g. UFM of Example 1<br>= 95 g. non-volatile<br>= 2 equivalents | 316 g. trimethyl<br>hexamethylene diamine<br>= two moles<br>a product of Huels,<br>formerly Veba | very light yellow transparent | 3.8 |
| 21 | 85 g. UFM of Example 1<br>= 47.5 g. non-volatile<br>= 1.0 equivalent | 129 g. N—aminoethyl piperazine<br>= one mole | water-white transparent | 3.15 |
| 22 | 130 g. UFM of Example 1<br>= 71 g. non-volatile<br>= 1.5 equivalents | 171 g. of water white distillate prepared from du Pont DACH, a mixture of about half 1,2 diamine cyclohexane, about one-quarter hexamethylene diamine, and remainder of related compounds including 2-methyl pentamethylene diamine. The original material is very dark, but the distallate is water white. | water-white transparent | 3.0 |
| 23 | 107 g. thiourea-formaldehyde monomer in methanol,<br>Example 2<br>= 51.5 g. non-volatiles<br>= 1.0 equivalent | 166 g. 70% hexamethylene diamine in water<br>= 116 g. 100% HMD<br>= 1.0 moles | water-white transparent | 4.0 |
| 24 | 85 g. UFM<br>= 47.5 g. non-volatile<br>= 1 equivalent | 136 g. m-xylene diamine<br>= 1 mole | water-white transparent | — |

Examples of cure of epoxy resins

The various urea-formaldehyde type polyamines were reacted with the standard epoxy resin—the diglycidyl ether of bisphenol A.

The curing reactions were all begun at room temperature, with the resulting exotherm uncontrolled.

The polyamine-to-epoxy-resin ratios shown in the examples below are only approximately stoichiometric and illustrate the curing ability of these new curing agents. For optimum results, one should vary the illustrated ratios in each instance and study the properties of the resulting films or castings, to arrive at the desired property or properties, or to achieve a desired compromise. These properties may be hardness, flexibility, chemical resistance, etc., obtaining either a maximum of one of these or the desired best overall aggregation of properties, for maximum results for one property does not necessarily mean maximum results for another property; so there may not be any one ratio at which the best results for all properties coincide.

TABLE II

| Example No. | UF Polyamine Per Example | Reactants and Proportions | Epoxy Curing Results | Properties of Cured Resin |
|---|---|---|---|---|
| 25 | diethylene triamine Example 6 | 30 g. liquid epoxy resin Dow DER 331<br>13 g. curing agent of Example 6 | Clear transparent mix at once. Exothermed very hot in 40 minutes. | Film on steel very tough |
| 26 | diethylene triamine Example 7 | Same as 25 above. | Same as 25 above. | Same as 25 above, but perhaps harder film |
| 27 | triethylene tetramine Example 8 | 50 g. DER 331<br>10 g. curing agent of Example 8 | Slightly cloudy mix at once. Exotherm hot in 40 minutes. | Very tough film |
| 28 | hexamethylene diamine Example 9 | 30 g. DER 331<br>10 g. of curing agent of Example 9 amine at 15° C. | Very transparent mix at once. Exotherm very, very hot in 45 minutes. | |
| 29 | hexamethylene diamine Example 10 | Same as 28 above | Same as 28 above. | |
| 30 | polyoxypropylene diamine MW 400 Example 11 | 30 g. DER 331<br>15 g. curing agent of Example 11 | Clear transparent mix. Mild exotherm in about 4 hours. | Excellent, transparent tough, fairly flexible, glossy film. |
| 31 | polyoxypropylene diamine MW 230 Example 12 | 30 g. DER 331<br>15 g. curing agent of Example 12 | Transparent mix. Slow but positive cure at room temperature. | |
| 32 | monoethanol amine Example 13 | 30 g. DER 331<br>15 g. of curing agent of Example 13 | Hazy mix, cured in 24 hours | Soft solid. |
| 33 | hexamethylene diamine Example 14 | 30 g. DER 331<br>15 g. of curing agent of Example 14 | Very hot exotherm in 40 minutes | Excellent film on steel. |
| 34 | oleyl diamine Example 15 | 30 g. DER 331<br>30 g. of curing agent of Example 15 | Made transparent mix at once. Mix applied to steel panel under water. Film cured under water in 24 hours. | |
| 35 | hexamethylene diamine Example 16 | 53 g. DER 331<br>18 g. of curing agent of Example 16 at 15° C. | Mix transparent at once. Very hot exotherm in 35 minutes. Applied to steel panel. Set to solid film in 2 hours. | In 24 Hours the film was glossy, transparent and very tough and hard. |
| 36 | polyoxypropylene triamine MW 400 Example 17 | 15 g. DER 331<br>30 g. of curing agent of Example 17 at 18° C. | | |
| 37 | poly (oxyethylene) diamine MW 600 Example 18 | 30 g. DER 331,<br>20 g. of curing agent of Example 18 | Very transparent water-white mix at once. | Very slow cure. Formed a soft casting in 10 days. |
| 38 | isophorone diamine Example 19 | 50 g. DER 331<br>20 g. of curing agent of Example 19 | Made transparent mix at once. Water-white. Hot exotherm in 60 minutes. | |
| 39 | trimethyl hexamethylene diamine Example 20 | 50 g. DER 331<br>20 g. of curing agent of Example 20 | Made transparent mix at once. Exotherm of 70° C. in 90 minutes. | |
| 40 | N—amino ethyl piperazine Example 21 | 60 g. DER 331<br>30 g. of curing agent of Example 21 | Made transparent mix at once. Very hot exotherm in 40 minutes. | Made hard film on an aluminum panel. |
| 41 | 1,2 diamine cyclohexane Example 22 | 30 g. DER 331<br>15 g. of curing agent of Example 22 | Made transparent mix at once. Hot exotherm in 40 minutes. | Made hard film on an aluminum panel. |
| 42 | 2,4 bis (p-aminobenzyl) aniline Example 5 | 20 g. DER 331<br>10 g. of curing agent of Example 5<br>5 g. benzyl alcohol | Transparent dark brown-red liquid on mixing, cured to hard casting in 24 hours. | Made excellent hard transparent glossy adhesive film on steel and on aluminum in 24 hours. |

TABLE II-continued

| Example No. | UF Polyamine Per Example | Reactants and Proportions | Epoxy Curing Results | Properties of Cured Resin |
|---|---|---|---|---|
| 43 | hexamethylene diamine Example 23 | 50 g. DER 331 20 g. of curing agent of Example 23 | Mix transparent at once. Hot exotherm in 35 minutes. | |
| 44 | m-xylene diamine Example 24 | 50 g. DER 331 20 g. of curing agent of Example 24 | Mix transparent at once. Hot exotherm in 35 minutes. | |

The invention having been described and exemplified, what I claim as my invention is:

1. A method for making a urea-formaldehyde polyamine compound for use in curing epoxy resins, comprising the steps of
   (a) reacting urea and paraformaldehyde in a lower alcohol under basic conditions and well above room temperature,
   (b) adding acid to make the reaction strongly acidic, with resulting exotherm,
   (c) holding the reaction at about 70°–120° C. for about an hour, and
   (d) bringing the pH to about 7.0,
   (e) removing the resulting urea-formaldehyde monomer, consisting mainly of urea-formaldehyde ether monomer, from the remaining material,
   (f) reacting each mole of the urea-formaldehyde ether monomer with about two to about four moles of an aliphatic, cycloaliphatic, or aromatic polyamine to split the ether group of the urea-formaldehyde ether molecule and form a carbon-nitrogen bond to an amine group at a site of the ether splitting.

2. The method of claim 1 wherein the urea-formaldehyde monomers include some methylol groups, comprising in step (f) also reacting the methylol groups with the polyamine.

3. The method of claim 2 wherein step (f) starts at about room temperature, rising somewhat due to exotherm.

4. The method of claim 2 followed by (g) distilling off the alcohol and water of reaction, to give a low-viscosity transparent liquid.

5. The method of claim 1 wherein step (f) starts at about room temperature rising somewhat due to exotherm.

6. The method of claim 1 followed by (g) distilling off the alcohol and water of reaction, to give a low-viscosity transparent liquid.

7. The method of claim 1, where the polyamine is

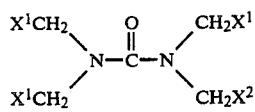

where $X^1$ is

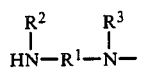

and $X^2$ is $X^1$ or

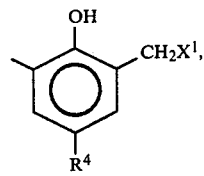

where $R^1$ is one of the following,

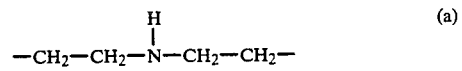 (a)

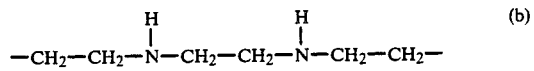 (b)

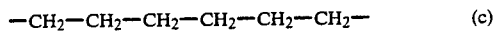 (c)

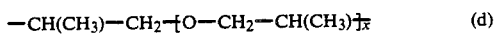 (d)

x varying from about 2 to about 6

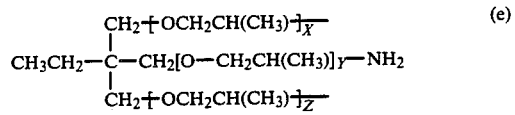 (e)

where $X+Y+Z=5.3$

 (f)

where $a+c=3.5$
and $b=13.5$

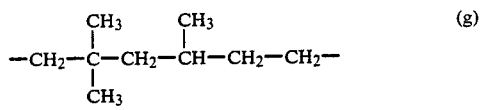 (g)

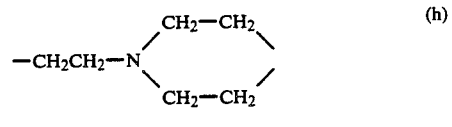 (h)

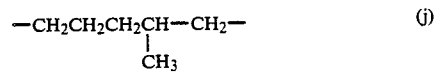 (i)

—CH$_2$CH$_2$CH$_2$CH—CH$_2$— (j)
              |
              CH$_3$

-continued

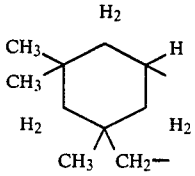 (k)

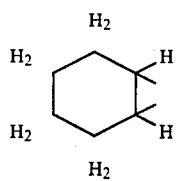 (l)

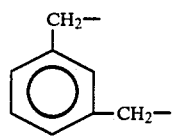 (m)

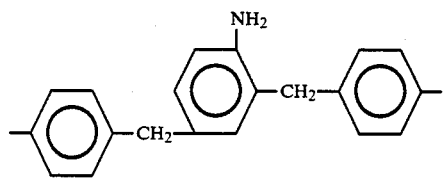 (n)

mixture of 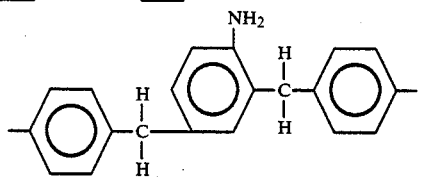 and (o)

—CH₂—CH₂—CH₂— (p)

$R^2$ and $R^3$ are both H where $R^1$ is any of (a) to (o) and when $R^1$ is (p), either $R^2$ or $R^3$, but not both, is $C_{18}H_{35}$, while the other is H, and $R^4$ is H or an alkyl radical with one to nine carbon atoms.

8. A method for making a thiourea-formaldehyde polyamine compound suitable for use in curing epoxy resins, comprising the steps of:
   (a) reacting thiourea and paraformaldehyde in a lower alcohol under basic conditions and and well above room temperature,
   (b) adding acid to make the reaction strongly acidic, with resulting exotherm,
   (c) holding the reaction at about 65° to 120° C. for about an hour, and
   (d) bringing the pH to about 7.0,
   (e) removing from the remaining material the resulting thiourea-formaldehyde monomer consisting mainly of thiourea-formaldehyde ether monomer,
   (f) reacting each mole of the thiourea-formaldehyde ether monomer with about two to about four moles of an aliphatic, cycloaliphatic polyamine or an aromatic polyamine to split the ether group of the thiourea-formaldehyde ether molecule and form a carbon-nitrogen bond to an amine group at the site of the ether splitting.

9. The method of claim 8 wherein the thiourea-formaldehyde monomers include some methylol groups, comprising in step (f) also reacting the methylol groups with the polyamine.

10. The method of claim 9 wherein step (f) starts at about room temperature, rising somewhat due to exotherm.

11. The method of claim 9 followed by (g) distilling off the alcohol and water of reaction, to give a low-viscosity transparent liquid.

12. The method of claim 8 wherein step (f) starts at about room temperature, rising somewhat due to exotherm.

13. The method of claim 8 followed by (g) distilling off the alcohol and water of reaction, to give a low-viscosity transparent liquid.

14. The method of claim 8 wherein the polyamine is hexamethylene diamine.

15. A method for making a phenolic substituted urea-formaldehyde polyamine compound suitable for use in curing epoxy resins, comprising the steps of:
   (a) reacting urea, an alkyl phenol having from 1 to 9 carbon atoms, and paraformaldehyde in a lower alcohol under basic conditions and well above room temperature,
   (b) adding acid to make the reaction strongly acidic, with resulting exotherm,
   (c) holding the reaction at about 65°–120° C. for about an hour, and
   (d) bringing the pH to about 7.0,
   (e) removing the resulting alkyl-phenol substituted urea-formaldehyde ether monomer from the remaining material,
   (f) reacting each mole of the alkyl-phenol substituted urea-formaldehyde ether monomer with about two to about four moles of an aliphatic or cycloaliphatic polyamine to split the ether group of the substituted urea-formaldehyde molecule and form a carbon-nitrogen bond to an amine group at the site of the ether splitting.

16. The method of claim 15 wherein the substituted urea-formaldehyde used in step (a) is nonyl phenol.

17. The method of claim 16 wherein step (f) starts at about room temperature, rising somewhat due to exotherm.

18. The method of claim 16 followed by (g) distilling off the alcohol and water of reaction, to give a low-viscosity transparent liquid.

19. The method of claim 16 where the polyamine in step (f) is hexamethylene diamine.

20. The method of claim 15 wherein the polyamine in step (f) is oleyl diamine.

21. The method of claim 15 wherein step (f) starts at about room temperature, rising somewhat due to exotherm.

22. The method of claim 15 followed by (g) distilling off the alcohol and water of reaction, to give a low-viscosity transparent liquid.

23. The method of claim 15 where the polyamine in step (f) is hexamethylene diamine.

24. A method for making a urea-formaldehyde amine compound suitable for use in curing epoxy resins, comprising the steps of:
   (a) reacting urea and paraformaldehyde in a lower alcohol under basic conditions and well above room temperature, (b) adding acid to make the reaction strongly acidic, with resulting exotherm,
(c) holding the reaction at about 70°–120° C. for about an hour, and
(d) bringing the pH to about 7.0,
(e) removing the resulting urea-formaldehyde ether monomer from the remaining material,
(f) reacting one mole of the urea-formaldehyde ether monomer with about four moles of monoethanol amine to split the ether group of the urea-formaldehyde ether molecule and form a carbon-nitrogen bond to an amine group at the site of the ether splitting.

* * * * *